United States Patent [19]

Matson et al.

[11] Patent Number: 4,786,597
[45] Date of Patent: Nov. 22, 1988

[54] METHOD AND APPARATUS FOR CONDUCTING CATALYTIC REACTIONS WITH SIMULTANEOUS PRODUCT SEPARATION AND RECOVERY

[75] Inventors: Stephen L. Matson, Schenectady, N.Y.; John A. Quinn, Merion Station, Pa.

[73] Assignee: University Patents, Inc., Westport, Conn.

[21] Appl. No.: 479,285

[22] Filed: Jun. 2, 1983

Related U.S. Application Data

[63] Continuation of Ser. No. 254,350, Apr. 15, 1981, abandoned.

[51] Int. Cl.$^4$ .................. C12P 1/00; B01J 19/24; C02F 1/44; C12M 1/40
[52] U.S. Cl. .................. 435/41; 422/238; 422/239; 210/638; 426/239; 435/287; 435/288; 435/813
[58] Field of Search .................. 435/41, 284, 287, 288, 435/803, 813, 819; 202/638; 426/239; 422/149, 236, 238, 239; 210/632, 638

[56] References Cited

U.S. PATENT DOCUMENTS

| | | | |
|---|---|---|---|
| 3,779,907 | 12/1973 | Li et al. | 210/638 |
| 3,827,565 | 8/1974 | Matsumura | 210/632 |
| 3,849,076 | 11/1974 | Gryaznov | 422/149 |
| 3,898,128 | 8/1975 | Chibata et al. | 195/29 |
| 4,014,785 | 3/1977 | Li et al. | 210/638 |
| 4,081,369 | 3/1978 | Li et al. | 210/638 |
| 4,119,408 | 10/1978 | Matson | 422/177 |
| 4,321,324 | 3/1982 | Maselli et al. | 435/813 |
| 4,324,767 | 4/1982 | Dines | 210/638 |

FOREIGN PATENT DOCUMENTS 1342869  1/1974  United Kingdom .............. 422/149

OTHER PUBLICATIONS

Zaborsky, "Immobilized Enzymes", CRC Press, Cleveland Ohio 44128, (1975) pp. 68, 69 and 132.

Primary Examiner—John E. Tarcza
Attorney, Agent, or Firm—George M. Yahwak

[57] ABSTRACT

Catalytic chemical and biochemical conversion reactions are carried out in a novel compartmentalized catalytic reactor which enables the energy-efficient coupling of the conversion reaction with various energy-consuming post-conversion operations. The catalytic reactor is compartmentalized by means of a multilayer composite membrane comprising a catalytic membrane layer and one or more permselective membrane layers. The arrangement and properties of the membrane layers are such as to enable the free energy change of the conversion reaction to be utilized as the required energy source for effecting various post-conversion operations, including product separation, recovery and enrichment, and second-stage catalytic conversions with unfavorable reaction equilibria.

12 Claims, 1 Drawing Sheet

METHOD AND APPARATUS FOR CONDUCTING CATALYTIC REACTIONS WITH SIMULTANEOUS PRODUCT SEPARATION AND RECOVERY

The present application is a continuation of my earlier filed U.S. patent application, Ser. No. 254,350, which was filed on Apr. 15, 1981, now abandoned.

BACKGROUND OF THE INVENTION

The invention described herein was made in the course of work under a grant or award from the National Science Foundation.

This invention relates to catalytic chemical and biochemical conversion reactions and, more particularly, to novel methods and apparatus for effecting energy-efficient coupling of such conversion reactions with various energy-consuming post-conversion operations.

In carrying out the various catalytic chemical and biochemical conversion reactions, the post-conversion product purification operations of separating, concentrating and recovering the desired end products from reaction mixtures containing unconverted reactants, undesired reaction byproducts, inerts, and catalysts, typically require an investment in plant which exceeds that associated with the reactor itself. Furthermore, an external source of energy is generally needed to accomplish these physical processes of product purification and recovery.

These factors present a particularly serious economic obstacle to the commercial application of the new recombinant DNA-based biotechnology requiring the purification and concentration of the products (e.g., antibiotics) of enzyme- or whole cell-catalyzed reactions from dilute aqueous fermentation broths, in that the cost of product recovery from such reaction mixtures can often be prohibitive.

The enormous expense involved in product purification and recovery from varied dilute fermentation broths, is partly explained by thermodynamics, since the isothermal reversible work required for recovery of the pure material from a mixture is roughly proportional to the logarithm of the reciprocal of the concentration in the mixture in which the substance is found or produced. For example, until recently, interferon was painstakingly recovered from blood, where it is present at an effective concentration of order 10 ppb by weight (approximately $10^{-11}$ mole fraction). Its estimated production cost by this method of 10–20 Billion Dollars per pound accurately reflects the difficulty of its purification. Yet another example of the central importance of separation costs in the bioprocessing arena is provided by biomass-derived ethanol, the net energy yield and economic viability of which depends largely on the development of efficient separation processes to replace distillation for alcohol recovery.

In many nonbiological catalytic chemical conversion processes, as well, the costs of product separation and concentration often determine whether or not a process is economically feasible. The conventional product separation and concentration techniques, such as distillation and crystallization, require one or more separate vessels in addition to the catalytic reactor, and in a typical chemical process, amount for 70 per cent of the capital investment and 80 per cent of the energy costs.

Another cost-limiting energy-consuming post-conversion operation frequently encountered in catalytic chemical or biochemical conversion processes, is the requirement for a second-stage catalytic conversion reaction in order to obtain the desired end product from an intermediate precursor thereof formed as the product of a first stage catalytic conversion reaction. Multi-stage catalytic conversion processes are the rule rather than the exception in biochemical systems, and conversion of raw materials to final products often occurs by a sequence of catalytic reactions in industrial chemistry as well. A commonly encountered process of this type is an overall thermodynamically favorable multi-stage catalytic conversion process comprising a first-stage catalytic conversion of a reactant to an intermediate precursor of the desired end product by means of a substantially irreversible thermodynamically favorable reaction, followed by a second-stage catalytic conversion of the intermediate precursor to the desired end product by means of a reversible thermodynamically unfavorable reaction. Despite the fact that the overall conversion of the initial reactant to the desired end product is thermodynamically favorable, the yield of the desired end product in a conventional reactor containing the first and second-state catalysts cannot exceed the small, equilibrium-limited conversion of the intermediate precursor to the desired end product. The resulting product stream would consist of a dilute solution of desired end product in more concentrated intermediate. This mixture would require separation of the end product from the intermediate, followed by recycle of the latter for further conversion. Associated with these steps are requirements for costly process equipment and energy consumption which might tend to render the process economically unfeasible.

Engineering research on membranes and membrane processes has been directed toward two primary objectives. The first, and by far the more extensively investigated, is the use of semipermeable membranes for separation purposes in so-called "extractive reaction" schemes, where the purpose of the membrane is to selectively remove the product of a reversible reaction from the reaction zone. The second, and more recent, membrane research objective is the use of membranes as solid supports for immobilizing otherwise soluble enzymes and homogeneous catalysts. Two-layer composite membrane structures combining a semipermeable membrane layer with a catalytic membrane layer, have previously been described as a wrap for an ion-specific electrode in analytical applications (Blaedel, et al., Analytical Chemistry, Vol. 47, No. 9, pages 1602–1608, August, 1975); and for enhancing the flux of a permeant (Tanny, et al., Journal of Membrane Science, Vol. 4, pages 363–377, 1979). However, these prior art applciations of such multilayer composite membranes have not involved catalytic conversion reaction flow systems enabling a catalytic conversion reaction to be advantageously coupled either with a post-conversion product separation, recovery and concentration scheme, or with a post-conversion second-stage catalytic conversion reaction in a multistage conversion reaction scheme.

SUMMARY OF THE INVENTION

It is, accordingly, a primary object of the present invention to provide new and improved methods and apparatus for carrying out catalytic chemical or biochemical conversion reactions which enable normally costly and energy-consuming post-conversion operations to be carried out in a more economical and energy-efficient manner.

Another object of the invention is to provide methods and apparatus in accordance with the preceding object, which enable the economical and energy-efficient separation, recovery and concentration of the desired end product resulting from the catalytic conversion reaction.

A further object of the invention is to provide methods and apparatus in accordance with the preceding objects, which enable economical and energy-efficient high overall conversions to be attained in multistage catalytic conversion reactions with unfavorable reaction equilibria.

Still another object of the invention is to provide methods and apparatus in accordance with the preceding objects, which are suitable for use in enzyme- or whole cell-catalyzed fermentation reactions.

The above and other objects are achieved in accordance with the present invention by providing a compartmentalized catalytic reactor adapted for conducting a catalytic chemical or biochemical conversion of a reactant present in a feed mixture to a desired end product and for simultaneously effecting separation and recovery of the desired end product from the reaction mixture. The catalytic reactor has a feed stream flow path and a product stream flow path extending in substantially parallel relation through the reactor on the opposite sides of a multilayer composite membrane comprising a feed stream-side permselective membrane layer interfacing with the feed stream flow path and a catalytic membrane layer adjacent to the feed stream-side permselective membrane layer. The catalytic membrane layer is composed of a microporous membrane having the conversion catalyst immobilized therein. The feed stream-side permselective membrane layer is permeable to the reactant and substantially impermeable to at least one reaction product selected from the group consisting of the desired end product and an intermediate precursor thereof. The product stream side of the composite membrane is permeable to the desired end product.

In accordance with one aspect of the invention, the above-described catalytic reactor may be utilized for conducting a catalytic chemical or biochemical conversion of a reactant present in a feed mixture to a desired end product so as to simultaneously effect separation of the desired end product from the reaction mixture and recovery of the desired end product in a more concentrated form than the initial reactant concentration in the feed mixture. This procedure is carried out by passing the feed mixture through the reactor along the feed stream flow path, whereby the reactant diffuses through the feed stream-side permselective membrane layer into the catalytic membrane layer where it becomes converted in one or more stages to the desired end product. The free energy change of the conversion reaction serves to drive the desired end product toward the product stream flow path. An inert sweep fluid is passed through the reactor along the product stream flow path at a flow rate lower than that of the feed mixture. This results in the desired end product separated from the reaction mixture and in a more concentrated form than the initial reactant concentration in the feed mixture being recovered as the product stream withdrawn from the poduct stream flow path.

Another aspect of the invention utilizes the above-described catalytic reactor in a process for conducting an overall thermodynamically favorable multistage catalytic chemical or biochemical conversion of a reactant present in a feed mixture to a desired end product, comprising a first-stage catalytic conversion of the reactant to an intermediate precursor of the desired end product by means of a substantially irreversible thermodynamically favorable reaction, followed by a second-stage catalytic conversion of the intermediate precursor to the desired end product by means of a reversible thermodynamically unfavorable reaction. The use of the catalytic reactor of the present invention enables the separation and recovery of the desired end product from the reaction mixture in high overall yield via thermodynamic and kinetic coupling of the first and second-stage conversion reactions. For this use, the multilayer composite membrane also includes a product stream-side permselective membrane layer interfacing with the product stream flow path, and the catalytic membrane layer, having both the first and second-stage conversion catalysts immobilized therein, is sandwiched between the feed stream-side and the product stream-side permselective membrane layers. The feed stream-side permselective membrane layer is permeable to the reactant, and the product stream-side permselective membrane layer is permeable to the desired end product, while both of the permselective membrane layers are substantially impermeable to the intermediate precursor. The process is carried out by passing the feed mixture through the reactor along the feed stream flow path, whereby the reactant diffuses through the feed stream-side permselective membrane layer into the catalytic membrane layer where it becomes sequentially converted first into the intermediate precursor and finally into the desired end product. The permselective membrane layers serve to confine the intermediate precursor within the catalytic membrane layer so as to enable the intermediat precursor concentration within the catalytic membrane layer to reach a kinetically favorable level for the second-stage conversion reaction. The free energy change of the first-stage conversion reaction serves to drive the second-stage conversion reaction to completion as well as to drive the desired end product toward the product stream flow path. An inert sweep fluid is passed through the reactor along the product stream flow path, whereby the desired end product separated from the reaction mixture is recovered in high overall yield as the product stream withdrawn from the product stream flow path.

By utilizing the free energy change of the conversion reaction for powering a post-conversion energy-consuming operation, and thereby coupling the post-conversion operation to the conversion reaction itself in a single piece of equipment, each of the two above-described procedures employing the catalytic reactor in accordance with the present invention, whether individually or in combination, result in increased efficiency of energy and equipment use. Furthermore, each of these two procedures are particularly suitable for use in carrying out enzyme- or whole cell-catalyzed fermentation reactions, thereby enhancing the commercial potential of the new recombinant DNA-based biotechnology.

BRIEF DESCRIPTION OF THE DRAWINGS

The various aspects of the present invention are illustrated in the accompanying drawings, wherein.

DESCRIPTION OF PREFERRED EMBODIMENTS

Figure 1:
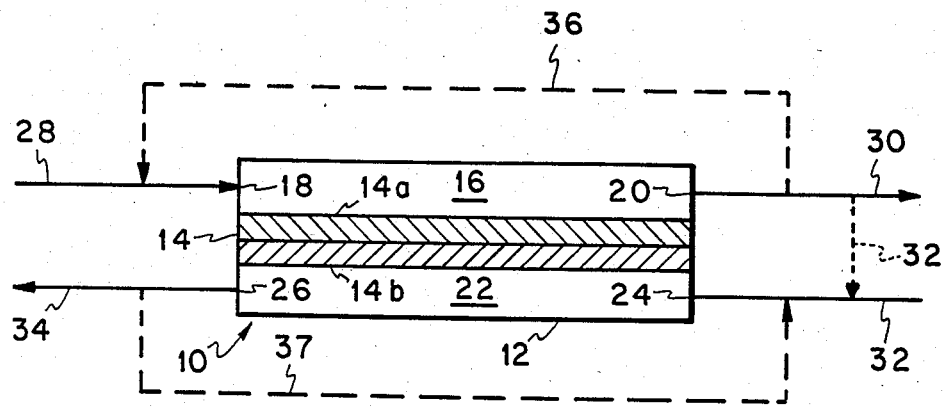
FIG. 1 is a schematic diagram of the compartmentalized catalytic reactor in accordance with the present invention, shown with a two-layer composite membrane and illustrating the general flow of materials therethrough when utilized for carrying out a catalytic conversion reaction with simultaneous separation and recovery of the desired end product from the reaction mixture.

Referring now to FIG. 1 of the drawings, a catalytic reactor 10 in accordance with the present invention is formed of a housing 12, and a multilayer composite membrane 14 supported within the housing 12 and extending across the length thereof. A feed stream flow channel 16 extends within the housing 12 along one surface of the composite membrane 14 from a feed stream inlet 18 to a feed stream outlet 20. A product stream flow channel 22 extends within the housing 12 in substantially parallel relation to the feed stream flow channel 16 along the opposite surface of the composite membrane 14 from a product stream inlet 24 to a product stream outlet 26. Auxiliary to the catalytic reactor 10 are feed stream inlet conduit 28 leading into the feed stream inlet 18, feed stream outlet conduit 30 leading from the feed stream outlet 20, product stream inlet conduit 32 leading into the product stream inlet 24, and product stream outlet conduit 34 leading from the product stream outlet 26. The feed stream outlet conduit 30 is optionally provided with a feed stream recycling conduit 36 leading into the feed stream inlet conduit 28, and a feed stream recycling conduit 38 leading into the product stream inlet conductor 32. While the product stream is shown in FIG. 1 in counter current flow with the feed stream, co-current flow can alternatively be used. The product stream outlet conduit 34 is optionally provided with a product stream recycling conduit 37 leading into the product stream inlet conduit 32.

Figure 2:
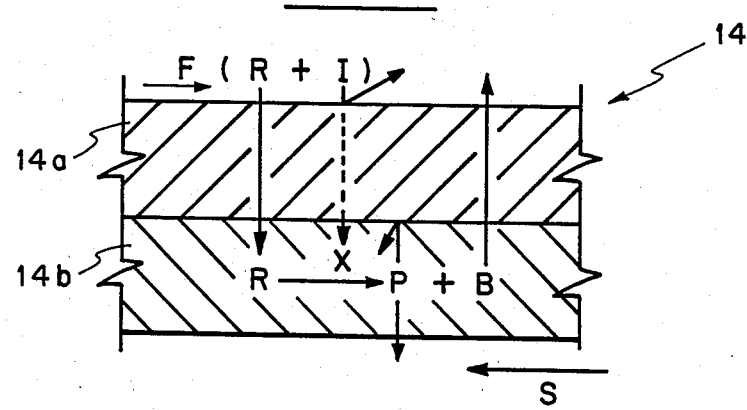
FIG. 2 is an enlarged fragmentary view of the two-layer composite membrane shown in FIG. 1, and illustrating the diffusion and interaction of materials therein during a single stage catalytic conversion reaction in accordance with the present invention.

The composite membrane 14 serves as a common wall between the feed stream flow channel 16 and the product stream flow channel 22. The composite membrane 14 is shown in FIGS. 1 and 2 as a two-layer composite membrane comprising a feed stream-side permselective membrane layer 14a interfacing with the feed stream flow channel 16, and a catalytic membrane layer 14b adjacent to the feed stream-side permselective membrane layer 14a and interfacing with the product stream flow channel 22. In an alternative embodiment shown in FIG. 3, a three-layer composite membrane 114 is formed with a feed stream-side permselective membrane layer 114a which interfaces with the feed stream flow channel 16, a product stream-side permselective membrane layer 114c which interfaces with the product stream flow channel 22, and a catalytic membrane layer 114b sandwiched between the feed stream-side permselective membrane layer 114a and the product stream-side permselective membrane layer 114c.

The catalytic membrane layer 14b or 114c is composed of a microporous membrane having the conversion catalyst or catalysts immobilized therein, for example, by phase differences or by any of several standard immobilization techniques, such as covalent bonding, crosslinking, gel entrapment, adsorption, or the like. The catalyst component of the membrane will depend upon the particular catalytic conversion being carried out, and may be either a biochemical conversion catalyst, such as enzymes or whole cells, or a synthetic homogeneous catalyst. For carrying out a multistage catalytic conversion reaction in accordance with the present invention, the three-layer composite membrane 114 will generally be used, with its catalytic membrane layer 114b including a plurality of conversion catalysts immobilized therein.

The permselective membrane layer 14a of the two-layer composite membrane 14, and each of the two permselective membrane layers 114a and 114c of the three-layer composite membrane 114, will typically be composed of a semipermeable membrane selected from the group consisting of immobilized liquid membranes (ILM's), ion exchange membranes (IEM's), and facilitated transport membranes. Particularly suitable semipermeable membranes for use as the permselective membrane layers in accordance with the present invention are immobilized liquid membranes consisting of a water-immiscible solvent for the particular reactant being employed, held by capillarity in a microporous hydrophobic support membrane. ILM's and IEM's are particularly suitable for reactions which form charged products from electrically neutral reactants; the difference in solubilities of electrolytes and non-electrolytes in organic solvents can be exploited to form ILM's of high selectivity, and Donnan exclusion of an electrolyte from an IEM is a second basis for selectivity. Finally, chemical reaction can introduce or remove functional groups, with the result that a highly selective facilitated transport system may be available either for reactant or for product.

The feed stream-side permselective membrane layers 14a and 114a should be selected so as to be permeable to the particular reactant employed, and substantially impermeable to at least one reaction product selected from the group consisting of said desired end product and an intermediate precursor thereof, depending upon whether the catalytic conversion reaction being carried out is a single stage conversion or a multistage conversion. When a single stage conversion is being carried out employing the two-layer composite membrane 14, the feed stream-side permselective membrane layer 14a should be substantially impermeable to the desired end product. When carrying out a multistage catalytic conversion reaction employing the three-layer composite membrane 114, on the other hand, the feed stream-side permselective membrane layer 114a should be substantially impermeable at least to the intermediate precursor of the desired end product formed in the reaction. In order to achieve useful degrees of product separation and enrichment, the feed stream-side permselective membrane layer preferably exhibits a separation factor between the reactant and the reaction product to which it is substantially impermeable of at least 10. When the feed mixture employed in the reaction contains one or more inert components, the permeability of the feed stream-side permselective membrane layer is preferably selective for the reactant in the feed mixture in relation to such inert components, so as to substantially maintain the inert components on the feed stream side of the membrane. Likewise, when one or more undesired reaction byproducts are formed in the conversion reaction, the feed stream-side permselective membrane layer is preferably permeable to such reaction by-products, so as to enable substantial diffusion thereof into the feed stream side of the membrane and thus be separated from the desired end product.

The product stream side of the composite membrane, i.e., the catalytic membrane layer 14b of the two-layer composite membrane 14, or the product stream-side permselective membrane layer 114c of the three-layer composite membrane 114, should be permeable to the desired end product so as to enable its diffusion into the product stream flow channel 22. When employing the three-layer composite membrane 114 for carrying out a multistage catalytic conversion reaction, the product stream-side permselective membrane layer 114c should be substantially impermeable to the intermediate precursor of the desired end product formed during the reaction.

The catalytic reactor 10 is utilized in the following manner for conducting a single stage catalytic conversion with simultaneous separation, recovery and concentration of the desired end product. Referring to FIGS. 1 and 2, a feed mixture F containing a reactant R and an inert component I is passed, via feed stream inlet conduit 28 and feed stream inlet 18, through the reactor 10 along the feed stream flow channel 16, whereby the reactant R diffuses through the feed stream-side permselective membrane layer 14a into the catalytic membrane layer 14b, where it becomes converted by means of conversion catalyst X to the desired end product P and an undesired byproduct B. Due to the fact that the ratio of the feedstream to product stream flow-rates is high, and secondarily due to the fact that the permeability of the feed stream-side permselective membrane layer 14a is selective for the reactant R in relation to the inert component I, the inert component I is maintained substantially on the feed stream side of the composite membrane 14. Furthermore, due to the fact that the feed stream-side permselective membrane layer 14a is permeable to the reaction byproduct B, at least most of the reaction byproduct B backdiffuses through the feed stream-side permselective membrane layer 14a into the feed stream. The substantial impermeability of the feed stream-side permselective membrane layer 14a to the desired end product P acts as a barrier to the backdiffusion of the desired end product P. The free energy change of the conversion reaction serves to drive the desired end product P toward the poduct stream flow channel 22. An inert sweep fluid S is passed, via product stream inlet conduit 32 and product stream inlet 24, through the reactor along the product stream flow channel 22. By maintaining the feed stream to product stream flow rate ratio greater than 1, preferably at least 5, and more preferably at least 10, the desired end product P seaprated from the reaction mixture and in a more concentrated form than the initial reactant R concentration in the feed mixture, is recovered as the product stream withdrawn from the product stream flow channel 22 through the product stream outlet 26 and the product stream outlet conduit 34.

Figure 3:
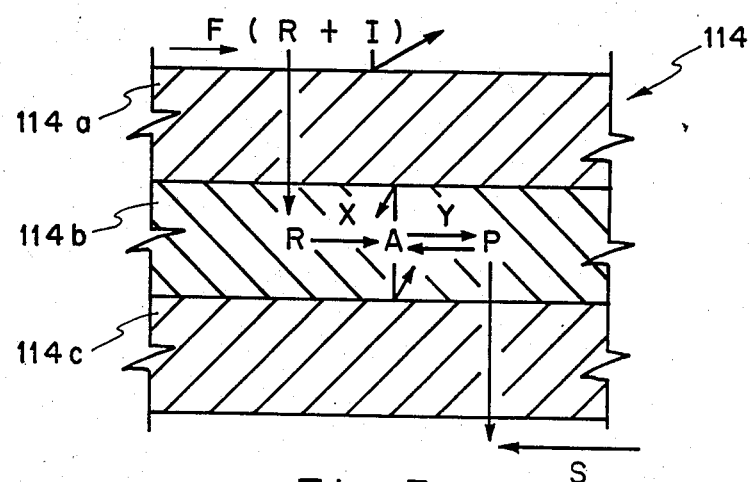
FIG. 3 is an enlarged fragmentary view similar to FIG. 2, and illustrating the diffusion and interaction of materials in a three-layer composite membrane during a two stage catalytic conversion reaction in accordance with the present invention.

Utilization of the reactor 10 for carrying out the multistage catalytic conversion process in accordance with the present invention, is effected in the following manner. Referring to FIGS. 1 and 3, the feed mixture F containing the reactant R and an inert component I is passed through the reactor 10 along the feed stream flow channel 16, as described above, whereby the reactant R diffuses through the feed stream-side permselective membrane layer 114a into the catalytic membrane layer 114b, where it becomes sequentially converted first into the intermediate precursor A by means of the first stage conversion catalyst X, and finally into the desired end product P by means of the second stage conversion catalyst Y. As discussed above, the inert component I is maintained substantially on the feed stream side of the composite membrane 114. The two permselective membrane layers 114a and 114c, being substantially impermeable to the imtermediate precursor A, serve to confine the intermediate precursor A within the catalytic membrane layer 114b so as to enable the intermediate precursor concentration within the catalytic membrane layer to reach a kinetically favorable level for the second stage conversion reaction. The free energy change of the first stage conversion reaction serves to drive the second stage conversion reaction to completion as well as to drive the desired end product P toward the product stream flow channel 22. An inert sweep fluid S is passed through the reactor 10 along the product stream flow channel 22, as discussed above, whereby the desired end product P separated from the reaction mixture is recovered in high overall yield as the product stream withdrawn from the product stream flow path.

In regard to this latter process, it should be noted that the feed stream-side permselective mémbrane layer 114a should exhibit a separation factor between said reactant R and said intermediate precursor A of the order of the reciprical of the equilibrium constant of the second stage conversion reaction in order to realize useful membrane reactor performance. A separation factor of at least 10 is particularly suitable.

While the methods and apparatus of the present invention are applicable to both chemical and biochemical catalytic conversion reactions, the most promising applications are biotechnology-related, in view of the good match which exists between the optimum operating conditions for membrane separations with those conditions at which biochemical conversions with enzymes or whole cells are conducted. Simply stated, presently available synthetic membranes are much more tolerant of aqueous environments, mild temperatures (25°–100° C.) and moderate pH ranges than they are of the organic solvents and extreme operating conditions which characterize other, non-biologically catalyzed chemical processes.

Representative enzymatic reactions which can suitably be carried out by means of the present invention include urea hydrolysis, the production of gluconic acid and urocanic acid, and the hydrolysis of benzyl penicillin with immobilized penicillin amidase to form 6-aminopenicillanic acid, the starting material in routes to the semi-synthetic penicillins.

In an alternative embodiment for carrying out the multistage catalytic conversion process in accordance with the present invention employing the three-layer composite membrane 114 shown in FIG. 3, the inert sweep fluid S may be replaced with additional feed mixture F passed through the product stream flow channel 22, preferably in concurrent flow with that being passed through the feed, stream flow channel 16. In this embodiment, the desired end product P will be recovered in each of the two streams withdrawn from the reactor 10, and further the permselective membrane layers 114a and 114c may have identical permeability properties.

We claim:

1. A method for conducting a catalytic chemical or biochemical conversion of a reactant present in a feed mixture to a desired end product so as to simultaneously effect separation of said desired end product from the reaction mixture and recovery of said desired end product in a more concentrated form than the initial reactant concentration in the feed mixture, comprising the steps of:

(a) providing a compartmentalized catalytic reactor having a feed stream flow path and a product stream flow path extending in substantially parallel relation through said reactor on opposite sides of a multilayer composite membrane comprising (1) a feed stream-side permselective membrane layer interfacing with said feed stream flow path and being permeable to said reactant and substantially impermeable to a reaction product and (2) a catalytic membrane layer adjacent to said feed stream-side permselective membrane layer, said catalytic membrane layer being composed of a microporous membrane having internal porous surfaces having immobilized thereon a conversion catalyst capable of irreversibly affecting conversion of said reactant to said desired end product within the presence of said conversion catalyst, and wherein the product stream side of said composite membrane is permeable to said desired end product;

(b) passing said feed mixture through said reactor along said feed stream flow path, whereby said reactant diffuses through said feed stream-side permselective membrane layer into said catalytic membrane layer where it becomes converted to said desired end product, the free energy change of the conversion reaction serving to drive said desired end product, said product subsequently diffusing toward said product stream flow path and (c) passing an inert sweep fluid through said reactor along said product stream flow path at a flow rate lower than that of said feed mixture, whereby said desired end product separated from the reaction mixture and in a more concentrated form than the initial reactant concentration in the feed mixture is recovered as the product stream withdrawn from said product stream flow path.

2. The method of claim 1, wherein said composite membrane is a two-layer membrane consisting of said feed stream-side permselective membrane layer and said catalytic membrane layer, said feed stream-side permselective membrane layer being substantially impermeable to said desired end product, said catalytic membrane layer interfacing with said product stream flow path.

3. The method of claim 2, wherein said feed stream-side permselective membrane layer is permeable to one or more reaction byproducts other than said desired end product, whereby at least most of said reaction byproducts backdiffuse through said feed stream-side permselective membrane layer into the feed stream.

4. The method of claim 1, wherein the permeability of said feed stream-side permselective membrane layer is selective for said reactant in relation to one or more inert components present in said feed mixture, whereby said inert components are maintained substantially on the feed stream side of said composite membrane.

5. The method of claim 1, wherein said conversion catalyst immobilized in said catalytic membrane layer is a biochemical conversion catalyst selected from the group consisting of enzymes and whole cells, and said catalytic conversion is a biochemical conversion.

6. The method of claim 5, wherein said catalytic biochemical conversion is a fermentation reaction.

7. The method of claim 1, wherein said feed stream-side permselective membrane layer exhibits a separation factor between said reactant and said reaction product to which it is substantially impermeable of at least ten.

8. The method of claim 1, wherein said feed steam-side permselective membrane layer is composed of a semipermeable membrane selected from the group consisting of an immobilized liquid membrane, an ion exchange membrane, and a facilitated transport membrane.

9. The method of claim 8, wherein said semipermeable membrane is an immobilized liquid membrane consisting of a water-immiscible solvent for said reactant held by capillarity in a microporous hydrophobic support membrane.

10. The method of claim 1, further including recycling of the feed stream from the outlet end of said feed stream flow path to the inlet end of either or both of said feed stream flow path and said product stream flow path.

11. The method of claim 1, wherein the feed stream to product stream flow rate ratio is at least 5.

12. The method of claim 11, wherein said flow rate ratio is at least 10.

* * * * *